United States Patent [19]
Bjorkholm

[11] Patent Number: 5,917,880
[45] Date of Patent: Jun. 29, 1999

[54] X-RAY INSPECTION APPARATUS

[75] Inventor: Paul J. Bjorkholm, Newport Beach, Calif.

[73] Assignee: EG&G Astrophysics, Long Beach, Calif.

[21] Appl. No.: 08/865,457

[22] Filed: May 29, 1997

[51] Int. Cl.⁶ .................................................. G01N 23/201
[52] U.S. Cl. .............................................. 378/57; 378/90
[58] Field of Search .................................. 378/57, 51, 53, 378/86, 87, 88, 89, 90

[56] References Cited

U.S. PATENT DOCUMENTS

| | | | |
|---|---|---|---|
| 4,228,351 | 10/1980 | Snow et al. | 378/90 X |
| 4,366,382 | 12/1982 | Kotowski | 378/57 |
| 4,768,214 | 8/1988 | Bjorkholm | 378/87 |
| 4,799,247 | 1/1989 | Annis et al. | 378/57 X |
| 4,819,256 | 4/1989 | Annis et al. | 378/87 |
| 4,933,961 | 6/1990 | Rushbrooke et al. | 378/57 |
| 4,956,856 | 9/1990 | Harding | 378/87 X |
| 5,247,560 | 9/1993 | Hosokawa et al. | 378/90 X |
| 5,247,561 | 9/1993 | Kotowski | 378/87 |
| 5,313,511 | 5/1994 | Annis et al. | 378/57 X |
| 5,347,122 | 9/1994 | Ansorge et al. | 250/227.11 |
| 5,428,657 | 6/1995 | Papanicolopoulos et al. | 378/90 X |
| 5,524,133 | 6/1996 | Neale et al. | 378/53 |
| 5,600,303 | 2/1997 | Husseiny et al. | 378/57 X |
| 5,600,700 | 2/1997 | Krug et al. | 378/57 |

OTHER PUBLICATIONS

*Port Technology International,* (Launch Edition) Section 3: Container Inspection Technology, pp. 89–109 (1995). no month.

*Primary Examiner*—David P. Porta
*Attorney, Agent, or Firm*—Peter J. Manus, Esq.

[57] ABSTRACT

An apparatus particularly suited to the inspection of carp in trucks, shipping containers and the like uses a beam of high energy x-rays, e.g., in the order of 8 Mev. A first detector is aligned with the beam to detect x-rays that have passed directly through the cargo. A second detector, located adjacent the first detector, receives x-rays that are inelastically forward scattered from the cargo at an angle in the range of 4° to 10°. Comparison of the relative amounts of x-ray received at each of these detectors with values for known materials identifies the nature of the cargo. The beam is fan-shaped and preferably vertical, and the detectors are preferably linear arrays of detector elements. Collimators define the field of view of the two detector arrays so that they both include a common spatial location within the cargo.

10 Claims, 3 Drawing Sheets

X-RAY INSPECTION APPARATUS

BACKGROUND OF THE INVENTION

The present invention relates to x-ray inspection apparatus and more particularly to x-ray inspection apparatus which provides an indication of the nature of the materials being inspected, i.e. by measuring line of sight atomic number. More specifically, the invention relates to an apparatus and methods for inspecting cargo held in containers such as trucks or standard shipping containers so as to detect and identify target materials such as explosives and contraband drugs.

Various non-destructive techniques for the inspection of closed containers using x-rays are described in the prior art. For example, U.S. Pat. No. 4,366,382 to Kotowski describes a widely used system for inspecting bags, luggage and the like at airports and buildings. A fan-shaped beam of x-rays irradiates the objects being inspected as they are carried through the beam on a conveyor. A linear array of detectors senses the attenuation produced by the objects on the interrogating x-ray beam and this attenuation information is processed electronically to produce a visual display of the objects. This display is typically referred to as a shadow-graph and while it is highly useful in detecting dense materials, e.g. metallic objects, it does not typically provide any information about the atomic composition of the materials being inspected.

The attenuation of an interrogating x-ray beam is due to the interaction of the x-ray photons with the electrons of the material forming the objects or objects in the path of the interrogating beam. At the low energy levels typically used for baggage inspection, e.g. 160 keV, this interaction is mainly due to both the photoelectric effect and to Compton scattering. In the photoelectric effect, the energy of the incident x-ray photon frees a bound electron. In Compton scattering, the x-ray photon collides with an electron resulting in a loss of energy from the photon with the photon travelling along an altered direction. At low energies, e.g. less than 1 MEV, there is substantial Compton scattering in virtually all directions, i.e. forward, side and back. However, at higher energy levels, e.g. in the order of 4 MEV and higher, the scattering becomes heavily forward biased, that is, the majority of photons are scattered at relatively small angles from the axis of the incident beam.

U.S. Pat. No. 5,247,561 to Kotowski describes a cargo scanning system using x-rays. It uses x-rays mainly in KeV range, but possibly as high as 4.0 MeV. Multiple linear arrays of photodetectors are arranged to detect Compton scattered radiation. Each detector "looks at", and is associated with, one volume element in the target.

A system for providing information regarding the nature of the materials being examined is disclosed in the Neale et al. U.S. Pat. No. 5,524,133. This system utilizes x-rays of two distinct and different energies to obtain additional information regarding the nature of the materials which the x-rays are interrogating. At least one energy is sufficiently high to interact through pair production. The system described employs two different sources which are spatially separated and indifferently oriented so as to avoid interference. The '133 patent also discloses various compound detectors that can be used to infer the spectral hardness of the transmitted beam and from this information infer the average atomic number of the material being inspected.

SUMMARY OF THE PRESENT INVENTION

Rather than employing two different interrogating energies or compound detectors, the present invention obtains information providing an indication of the nature of the materials being inspected by employing a single source of relatively high energy x-rays together with measurements of both on-axis attenuation and small angle forward scattered x-rays which have passed through the materials. These measured scatter and transmitted energy images can be used to determine the average atomic number of the material being inspected and from these data the detection of explosives and drugs despite the large amounts of metal typically associated with trucks and shipping containers. Briefly, x-ray inspection apparatus in accordance with the present invention employs a source providing a beam of x-rays having energies in excess of 4.0 MeV, and preferably on the order of 8 MEV. Materials to be inspected are passed through the beam while a first detector, aligned with the beam, receives x-rays from the source which have passed directly through the materials. A second detector adjacent the first detector receives x-rays from the source which are forward scattered from the materials being inspected by a small angle. A display provides an indication which varies as a function of the relative amounts of x-rays received by the first and second detectors thus providing also an indication of the nature of the materials through which the x-rays have passed.

BRIEF DESCRIPTION OF THE DRAWINGS

Corresponding reference characters indicate corresponding parts throughout the several views of the drawings.

DESCRIPTION OF THE PREFERRED EMBODIMENT

Figure 1:
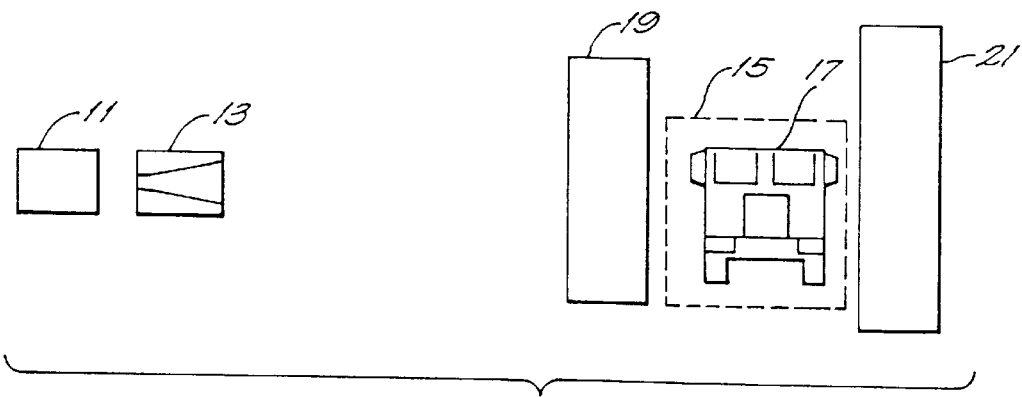
FIG. 1 is a front view of x-ray inspection apparatus in accordance with the present invention.
Figure 2:
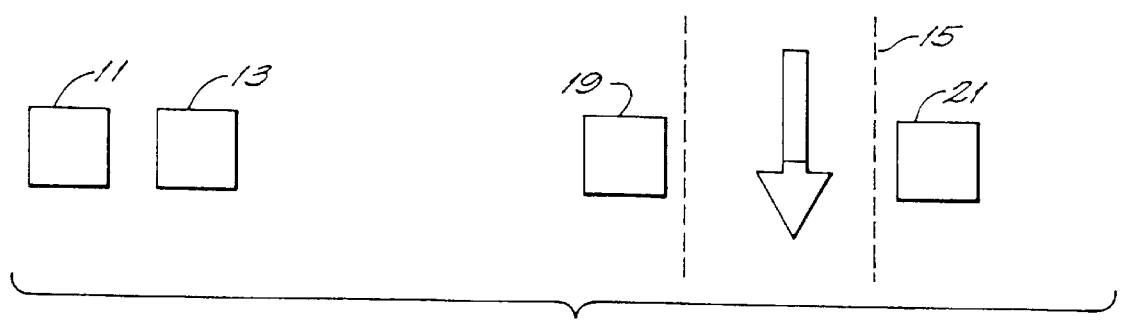
FIG. 2 is a top view of the apparatus of FIG. 1.

Referring now to FIGS. 1 and 2, an x-ray source 11 acts as a source providing x-rays at energies in the order of 8 MEV. The source 11 may be a Linatron or other source of high energy radiation. While the invention can operate with interrogating energies in excess of 10 MeV, this is the highest practical upper limit due to radiation safety regulations. The x-rays provided by the source 11 are formed into a fan beam by a first collimator 13. A tunnel 15 is provided through which cargo containing trucks 17, cargo containers or the like may be moved for x-ray interrogation. A further collimator 19 is preferably provided on the source side of tunnel 15 for further defining the beam so as to interrogate a vertical slice through the truck. On the opposite side of the tunnel 15 is provided a detector array with associated collimators, designated by reference character 21 and described in greater detail hereinafter.

Figure 3:
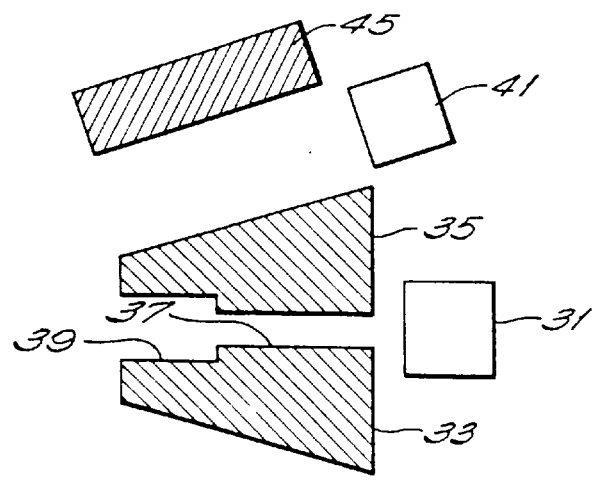
FIG. 3 is a top view, in section, of the detector arrays employed in the apparatus of FIGS. 1 and 2.

Referring now to FIG. 3, an on-axis detector array is designated by reference character 31. As is understood, this array may comprise a plurality of detector crystal elements, each with an associated photodetector diode. The detector elements are arranged in a vertical strip so as to receive x-rays from the fan-shaped beam which pass directly through the materials being inspected.

Just in front of the detector array 31 is a collimator structure comprising absorbing elements 33 and 35 which define therebetween a narrow slot 37 through which x-rays can reach the detector array 31. Preferably, a wider slot 39 is provided in front of the final beam defining slot 37, this deeper, wider slot serving to prevent interference by radiation scattered back into the tunnel from the elements 33 and 35 which might otherwise interfere with the detection of shallow angle forward scattered radiation.

A second detector array 41, essentially similar to the array 31, is provided for detecting x-rays which are forward scattered from the materials being inspected by a small angle, e.g. in the order of 4° to 10°. A further collimator element 45 working in conjunction with the collimator element 35 essentially confines the field of view of the detector array 41 so that it receives x-radiation essentially from the same material as that through which the direct radiation passes to the detector array 31 and not from the walls of the tunnel. The exact angular location of the second detector array 41 can vary somewhat to accommodate the presence of collimator 35. The optimal location can be determined empirically. The angle must be large enough to separate the detector arrays 31 and 41 functionally, but small enough that the array 41 measures the scattered energy cross section directly.

Figure 4:
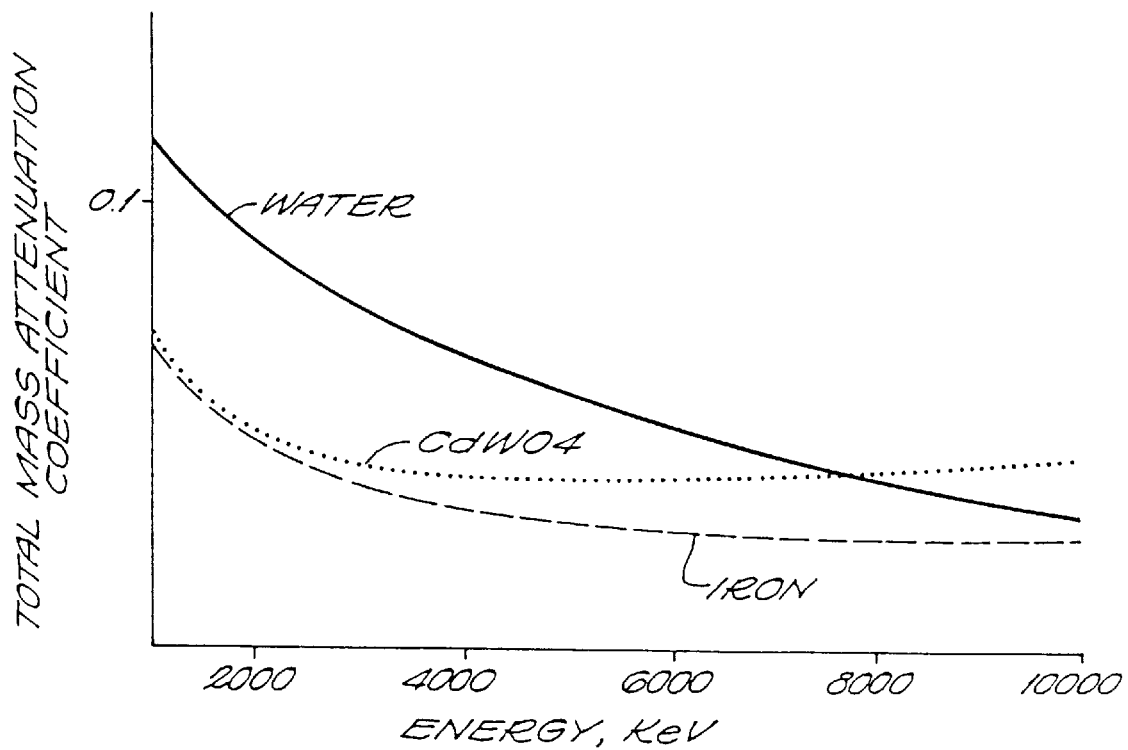
FIG. 4 is a chart graph of the total mass attenuation coefficient versus energy for three materials.

The invention is, in one sense, a technique to determine the average atomic number of the attenuating material in high energy material or cargo scanning. Prior art systems have, in effect, attempted to measure the spectral hardness of a transmitted x-ray beam and from that infer the atomic number of the attenuator. FIG. 4 shows the mass attenuation coefficient of water, iron, and cadmium tungstate in the energy region of 1 to 10 MeV. As may be seen the mass attenuation coefficient for water is a monotonically decreasing function of energy, for iron it decreases from 1 to 4 MeV and is approximately level from there to 10 MeV, and for cadmium tungstate it decreases from 1 to 4 MeV and increase thereafter. It can thus be seen that if a broad spectrum of x-rays were incident on these three materials the exit spectrum would be different. It is this difference that the prior art attempts to measure by using composite detectors.

The two competing processes that account for the difference in the mass attenuation coefficients are Compton scattering and pair production. It is the reletive weight of these two processes that accounts for the differences in the shape of the mass attenuation coefficient as a function of energy for various materials. What is significant in determining the nature of the material being scanned is the relative weight of the two processes.

In contrast with the prior art approaches, the present invention essentially directly measures the amount of scattering. This direct determination of scattering becomes practical only at high energies for two reasons; 1) at high energies the angular distribution of scattered photons is strongly forward peaked, and 2) the radiation coming from pair production is uniformly distributed. Therefore, in accordance with the presently understood theory of operation of the present invention, if one measures the amount of forward scatter, one gets a direct measurement of the relative strength of the Compton cross section to the total cross section.

Figure 6:
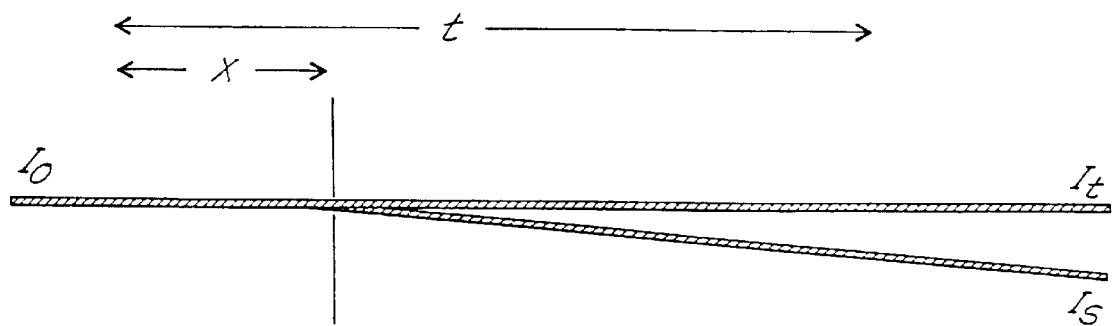
FIG. 6 is a diagram illustrating forward Compton scattering.

To compute the amount of scatter seen when transiting an object, the scatter from each location must be summed. This can be done using an integral. In that case the amount of scatter, $I_s$, is given by:

$$I_S = \int_0^t I_0 \cdot e^{-\mu\rho x} \cdot \sigma_c \cdot \rho_e \cdot G e^{-\mu\rho(t-x)} \, dx$$

where
t=thickness
$I_O$=incident energy spectrum
M=crossection (a function of E and Z )
E=Energy
Z=Atomic Number
P=density
$O_c$=Compton crossection
$P_e$=electron density
G=Geometric factor
See also FIG. 6.

However, combining the exponential terms the x dependence goes away so that $$I_s = I_t \sigma_c \rho_e G t$$

That is, the amount of scatter is proportional to the amount of transmitted beam times the Compton cross section times the electron density times a geometric factor (which depends totally on the target and on the detector size and shape) times the thickness of the target. This result is approximate because the energy dependence of the mass attenuation coefficient and the differences in path between the transmitted and scattered beams have been neglected. However, the mass attenuation coefficient is a relatively slow function of energy and for the small scattering angles to be considered here, the difference in energy between the scattered and transmitted photons is small. In addition, for large scale objects there is very little difference between the materials seen on the two paths.

To verify the above result, the Monte Carlo routine can be used to compute the amount of scatter and transmission as a function of thickness for two materials, water and iron. The result is the ratio of the scattered to transmitted radiation appears to be fairly linear with the thickness of the x-rayed object. However, this analysis is, in itself, not useful to determine the atomic composition of the object because it assumes that thickness is known. In cargo inspection, one typically does not know the thickness.

However, if one takes the equation for the transmission of x-rays and solves for the thickness of the material and replaces t in the equation for the scatter, the following is obtained.

$$I_s = I_t \sigma_c \rho_e G(-1n(I_t)/\mu\rho)$$

Regrouping, it can be shown that the amount of scatter is proportional to the amount of transmitted radiation times the natural log of the amount of scattered radiation times a factor that is proportional to the ratio of the Compton cross section to the total mass attenuation coefficient.

$$I_s \approx -I_t 1n(I_t) K \sigma_c/\mu$$

where k is a constant. Again using Monte Carlo data, the ratio of scatter to the transmission times the log of the transmission is shown in FIG. 5.

Figure 5:
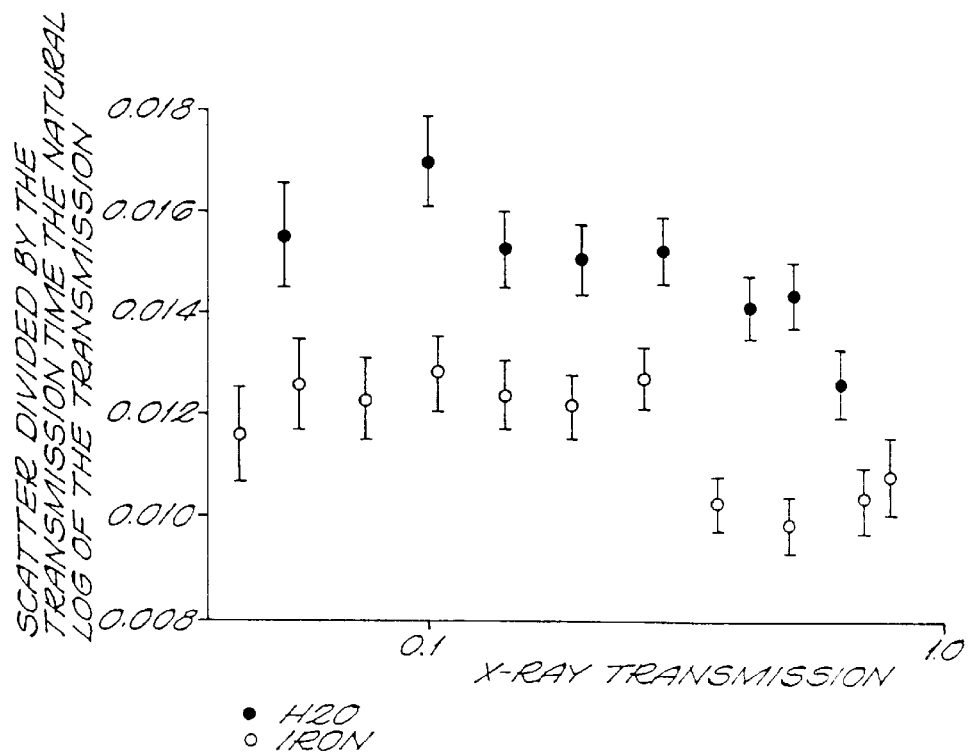
FIG. 5 is a chart illustrating the ratio of scatter to transmission times the log of the transmission.

The separation of the materials from the above data and analysis as illustrated in FIG. 5 is readily apparent. The error bars associated with each point are approximately the error bars to be expected from one pixel of the image. In other words the separation becomes more statistically significant as one aggregates pixels for determination of the atomic number of large areas of the image.

Thus, in one sense, the invention is the measurement of the average atomic number of attenuating material in a high energy material scanner by simultaneously measuring the amount of forward scattered radiation and the amount of transmitted radiation.

Each of the detector arrays 31 and 33 is electronically scanned or sampled repeatedly as the truck is moved through the tunnel 15. Preferably, the data obtained in this manner are presented in two different video displays. Firstly, as an energy image, i.e. shadow graph, obtained directly from the data obtained from the first detector array 31. A second video display can then present an image which provides an indication of the nature of the material which has been interrogated. As is understood, so-called false color presentations are particularly useful in this manner. Values to control the color can either be calculated in accordance with the theoretical description presented hereinbefore or may simply be obtained from a lookup table (LUT) which has been generated empirically by scanning target materials of different compositions and natures. In the case of a lookup table, the on-axis and forward scattered measurement values are used as entry indices into the lookup table.

In view of the foregoing it may be seen that several objects of the present invention are achieved and other advantageous results have been attained.

As various changes could be made in the above constructions without departing from the scope of the invention, it should be understood that all matter contained in the above description or shown in the accompanying drawings shall be interpreted as illustrative and not in a limiting sense. For example, while one second detector array 41 is shown and described, it will be understood that a second, mirror image array 41 can be used on the opposite side of the target beam to provide an additional direct reading of the attenuation due to scattering.

What is claimed is:

1. X-ray inspection apparatus providing an indication of the nature of the materials being inspected, said apparatus comprising:
    a source providing a beam of x-rays having energies in the order of 8 Mev;
    means for passing materials to be inspected through said beam;
    a first detector aligned with said beam for receiving x-rays from said source which pass directly through said materials;
    a second detector adjacent said first detector for receiving x-rays from said source which are inelastically forward scattered from materials being inspected by a small angle;
    a display providing an indication which varies as a function of the relative amounts of x-rays received by said first and second detectors.

2. Apparatus as set forth in claim 1 wherein said beam is fan shaped and vertically aligned.

3. Apparatus as set forth in claim 2 wherein said first and second detectors are each vertical arrays of detector elements.

4. Apparatus as set forth in claim 3 wherein said first and second detector arrays are provided with collimating elements containing the field of view of each of the arrays to a common spatial location through which said materials are passed.

5. Apparatus as set forth in claim 1 wherein said small angle is in the range of 4° to 10°.

6. Apparatus as set forth in claim 1 wherein said small angle is in the order of 5°.

7. Apparatus for inspecting cargo in containers to detect at least one selected type of material within the cargo, comprising:
    a source providing a fan beam of high energy radiation incident upon the cargo as said fan beam interrogates successive slices of the cargo through a relative movement of the fan beam with respect to the cargo,
    a first detector positioned in substantially direct alignment with the said fan beam and adapted to receive the radiation as attenuated by interaction with said slice of the cargo;
    a second detector positioned to receive forwardly scattered radiation as attenuated by interaction with said portion, principally through Compton scattering, thereby directly measuring the contribution of Compton scattering; and
    means for measuring the attenuated radiation received at said first and second detectors; and
    means for comparing these values to known values for known materials to detect at least one selected material.

8. Apparatus as set forth in claim 7 wherein said radiation comprises x-rays in the order of 8 Mev.

9. Apparatus as set forth in claim 7 wherein said first and second detector arrays are provided with collimating elements containing the field of view of each of the arrays to a common spatial location through which said materials are passed.

10. Apparatus as set forth in claim 7 wherein said second detector receives radiation which is off the axis of said beam by, an angle in the order of 5°.

* * * * *